United States Patent [19]

Kameswaran

[11] Patent Number: 5,130,328
[45] Date of Patent: Jul. 14, 1992

[54] N-ALKANOYLAMINOMETHYL AND N-AROYLAMINOMETHYL PYRROLE INSECTICIDAL AND ACARICIDAL AGENTS

[75] Inventor: Venkataraman Kameswaran, Princeton Junction, N.J.

[73] Assignee: American Cyanamid Company, Stamford, Conn.

[21] Appl. No.: 755,935

[22] Filed: Sep. 6, 1991

[51] Int. Cl.$^5$ ............... A01N 43/36; C07D 405/02; C07D 409/02; C07D 207/30
[52] U.S. Cl. .................... 514/426; 548/557; 548/558; 548/561; 548/527; 548/517
[58] Field of Search ............ 548/561, 557, 558, 527, 548/517; 514/426, 428

[56] References Cited

U.S. PATENT DOCUMENTS 4,798,901  1/1989  Tessier et al. ............ 548/557
5,010,098  4/1991  Brown et al. ............. 548/557

Primary Examiner—Mary C. Lee
Assistant Examiner—Joseph K. McKane
Attorney, Agent, or Firm—John W. Hogan, Jr.

[57] ABSTRACT

This invention relates to N-alkanoylaminomethyl and N-aroylaminomethyl pyrrole compounds. It also relates to the use of said compounds as insecticidal and acaricidal agents and to a method of protecting plants from attack by insects and acarina by application of an N-alkanoylaminomethyl or N-aroylaminomethyl pyrrole to said plants or to the locus in which they are growing.

8 Claims, No Drawings

N-ALKANOYLAMINOMETHYL AND N-AROYLAMINOMETHYL PYRROLE INSECTICIDAL AND ACARICIDAL AGENTS

SUMMARY OF THE INVENTION

The present invention relates to N-alkanoylaminomethyl and N-aroylaminomethyl pyrroles that are highly effective insecticidal and acaricidal agents useful for the control of insect and acarid pests and for protecting agronomic crops from the ravages of said pests.

The N-alkanoylaminomethyl and N-aroylaminomethyl pyrroles of the present invention have the structural formula I

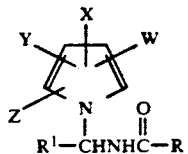

wherein
W is halogen, CN or $NO_2$;
X is halogen or phenyl optionally substituted with one or two halogen, CN, $NO_2$, $C_1$-$C_4$ alkyl, $C_1$-$C_4$ alkoxy or $CF_3$ groups;
Y is halogen, $CF_3$ or phenyl optionally substituted with one or two halogen, CN, $NO_2$, $C_1$-$C_4$ alkyl, $C_1$-$C_4$ alkoxy or $CF_3$ groups;
Z is halogen or $CF_3$;
$R_1$ is hydrogen or $C_1$-$C_4$ alkyl; and
R is $C_1$-$C_6$ alkyl optionally substituted with one to three halogen atoms,
  phenyl optionally substituted with one or two halogen, CN, $NO_2$, $C_1$-$C_4$ alkyl, $C_1$-$C_4$ alkoxy or $CF_3$ groups,
  2- or 3-thienyl or
  2- or 3-furyl;
provided that when W is halogen, then X is phenyl optionally substituted with one or two halogen, CN, $NO_2$, $C_1$-$C_4$ alkyl, $C_1$-$C_4$ alkoxy or $CF_3$ groups and Y and Z are $CF_3$.

DESCRIPTION OF THE PREFERRED EMBODIMENTS

The N-alkanoylaminomethyl and N-aroylaminomethyl pyrroles of this invention are excellent insecticidal and acaricidal agents. The present invention provides a method for controlling undesirable pests by applying a pesticidally effective amount of an N-alkanoylaminomethyl or N-aroylaminomethyl pyrrole to the breeding grounds, food supply or habitat of said pests.

Preferred formula I compounds are those in which
W is CN or $NO_2$;
X is phenyl optionally substituted with one or two halogen, CN, $NO_2$, $C_1$-$C_4$ alkyl, $C_1$-$C_4$ alkoxy or $CF_3$ groups;
Y is halogen or $CF_3$;
Z is halogen or $CF_3$;
$R_1$ is hydrogen; and
R is $C_1$-$C_6$ alkyl optionally substituted with one to three halogen atoms,
  phenyl optionally substituted with one or two halogen, CN, $NO_2$, $C_1$-$C_4$ alkyl, $C_1$-$C_4$ alkoxy or $CF_3$ groups,
  2- or 3-thienyl or
  2- or 3-furyl.

Other formula I compounds which are especially effective as insecticidal and/or acaricidal agents are those in which
W is CN or $NO_2$;
X is phenyl optionally substituted with one or two halogen or $CF_3$ groups;
Y is Cl, Br or $CF_3$;
Z is Cl, Br or $CF_3$;
$R_1$ is hydrogen; and
R is $C_1$-$C_6$ alkyl optionally substituted with one to three halogen atoms,
  phenyl optionally substituted with one or two halogen, $C_1$-$C_4$ alkyl, $C_1$-$C_4$ alkoxy or $CF_3$ groups, or
  2- or 3-thienyl.

The N-alkanoylaminomethyl and N-aroylaminomethyl pyrroles of this invention, as depicted by formula I, can be prepared from the appropriately substituted N-hydrogen pyrroles described in U.S. patent application Ser. No. 392,495 filed on Aug. 11, 1989; Ser. No. 600,054 filed on Oct. 18, 1990; Ser. No. 430,601 filed on Nov. 6, 1989; and Ser. No. 621,162 filed on Nov. 30, 1990 and are incorporated herein by reference thereto.

Preparation of the N-alkanoylaminomethyl and N-aroylaminomethyl pyrroles of the invention generally involves the alkylation of a pyrrole having the structural formula II

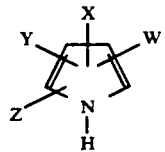

wherein W, X, Y and Z are as described for formula I above.

Alkylation of the formula II pyrrole can be achieved by the reaction of said formula II pyrrole with an alkali metal hydride or alkali metal $C_1$-$C_6$ alkoxide and an alkylating agent having the structural formula III

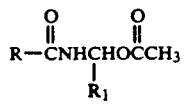

wherein R and $R_1$ are as described above for formula I.

In the reaction an alkali metal hydride such as sodium hydride or an alkali metal $C_1$-$C_6$ alkoxide such as potassium t-butoxide is generally dispersed in an anhydrous organic solvent such as dry tetrahydrofuran which contains the formula II pyrrole compound. The thus formed mixture is then added to a mixture of the formula III alkylating agent in an anhydrous organic solvent such as tetrahydrofuran. Thereafter, the thus prepared mixture is heated to refluxing temperatures until the N-alkanoylaminomethyl or N-aroylaminomethyl pyrrole is formed. The reactions are preferably conducted under a blanket of inert gas such as nitrogen or argon. The reaction scheme is shown below in Flow Diagram I:

FLOW DIAGRAM I

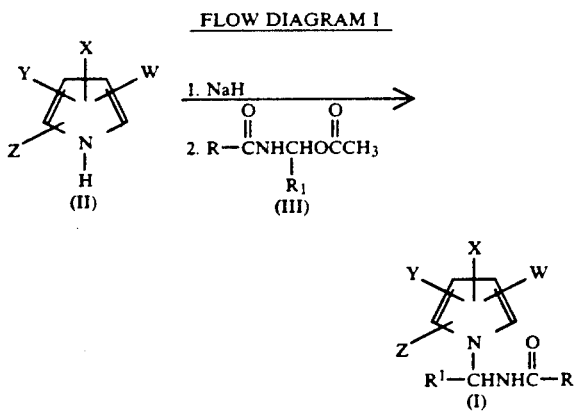

The N-alkanoylaminomethyl and N-aroylaminomethyl pyrroles of the present invention are effective for controlling insects and acarina. These compounds are also effective for protecting growing or harvested crops from attack by the above-said pests.

In practice generally about 10 ppm to 10,000 ppm and preferably 100 ppm to about 5,000 ppm of a formula I N-alkanoylaminomethyl or N-aroylaminomethyl pyrrole, dispersed in water, or another inexpensive liquid carrier, is effective when applied to the plants, the crops or the soil in which said crops are growing to protect said crops from attack by insects and/or acarina.

The formula I N-alkanoylaminomethyl and N-aroylaminomethyl pyrroles of this invention are also effective for controlling insects and acarina when applied to the foliage of plants and/or to the soil or water in which said plants are growing in sufficient amount to provide a rate of from about 0.1 kg/ha to 4.0 kg/ha of active ingredient.

While the N-alkanoylaminomethyl and N-aroylaminomethyl pyrroles of this invention are effective for controlling insects and acarina when employed alone, they may also be used in combination with other biological chemicals, including other insecticides and acaricides. For example, the N-alkanoylaminomethyl and N-aroylaminomethyl pyrroles of this invention may be used effectively in conjunction or combination with phosphates, carbamates, pyrethroids, formamidines, chlorinated hydrocarbons, halobenzoylureas and the like.

Advantageously, the above-said N-alkanoylaminomethyl and N-aroylaminomethyl pyrroles may be formulated into dry compacted granules, suspension concentrates, wettable powders, dusts, dust concentrates, emulsifiable concentrates, granular formulations, flowable compositions, micro-emulsions and the like, all of which lend themselves to soil, water and/or foliage application and provide the requisite plant protection. Such formulations include the compounds of the invention admixed with inert, pharmacologically-acceptable solid or liquid diluents.

A typical suspension concentrate formulation may be prepared by grinding together about 5% to 25% by weight of a formula I N-alkanoylaminomethyl or N-aroylaminomethyl pyrrole, about 3% to 20% by weight of an anoinic surfactant such as dodecyl benzene sulfonic acid, about 1% to 5% by weight of a nonionic surfactant such as an ethylene oxide block copolymer having about 8 to 11 mols of ethoxylation, about 1% to 5% by weight of an alkylphenol polyethylene oxide condensate with 9 to 10 mols of ethoxylation and q.s. to 100% with a petroleum aromatic solvent.

Wettable powders, dusts and dust concentrate formulations of the invention can be prepared by grinding together about 3% to 20%, by weight, of the formula I N-alkanoylaminomethyl or N-aroylaminomethyl pyrrole, with about 3% to 20% by weight of a solid anionic surfactant. One suitable anionic surfactant is a dioctyl ester of sodium sulfosuccinic acid, specifically Aerosol OTB® surfactant, marketed by the American Cyanamid Company. About 60% to 94%, by weight, of an inert solid diluent, such as montmorillonite, attapulgite, chalk, talc, kaolin, diatomaceous earth, limestone, silicates or the like also is used in such formulations.

Compacted granules especially useful for soil or water application can be prepared by grinding together in about equal parts, usually about 3 to 20 parts of the N-alkanoylaminomethyl or N-aroylaminomethyl pyrrole and a solid surfactant, with about 60 to 94 parts of gypsum. Thereafter, the mixture is compacted into small granular particles, about 24/48 mesh or larger.

Other suitable solid surfactants useful in the present formulations include not only the anionic dioctyl ester of sodium sulfosuccinic acid but also nonionic block copolymers of ethylene oxide and propylene oxide. Such block copolymers are marketed by BASF Wyandotte Corporation as Pluronic 10R8, 17R8, 25R8, F28, F68, F77, or F87, and are especially effective for the preparation of compacted granules.

In addition to the powders and concentrate formulations described hereinabove, wettable powders and flowables may be used because they may be dispersed in water. Preferably, such flowables will be applied at the locus with the aqueous compositions being sprayed on the foliage of plants to be protected. These sprays also may be applied to the breeding ground, food supply or habitat of the insects and acarina sought to be controlled.

Where solid formulations of the compounds of this invention are to be used in combination treatments with other pesticidal agents, the formulations can be applied as an admixture of the components or may be applied sequentially.

Similarly, liquid formulations of the N-alkanoylaminomethyl and N-aroylaminomethyl pyrroles in combination with other pesticidal agents may be tank mixed or may be applied separately, sequentially, as liquid sprays. Liquid spray formulations of the compounds of the invention should contain about 0.001% to 0.1% by weight of the active N-alkanoylaminomethyl or N-aroylaminomethyl pyrrole.

Surprisingly, in addition to their utility as effective insecticidal and acaricidal agents, the formula I compounds of this invention can be converted into formula IV N-halomethyl pyrroles which can then be converted into formula V N-alkoxymethyl pyrrole compounds. Advantageously, this process for converting formula I compounds into formula V N-alkoxymethyl pyrrole compounds avoids the use of certain undesirable reactants such as chloromethyl ethyl ether. The N-alkoxymethyl pyrrole compounds are particularly effective for controlling insect, acarid and nematode pests and for protecting agronomic crops, both growing and harvested, against the ravages of these pests. Formula IV N-alkoxymethyl pyrroles are prepared by reacting a formula I N-alkanoylaminomethyl or N-aroylaminomethyl pyrrole with an excess of phosphorus oxychloride or phosphorus oxybromide at reflux temperature. The thus obtained formula IV compound is then reacted with an alkali metal $C_1$–$C_6$ alkoxide such as sodium ethoxide in the presence of an inert organic solvent such as tetrahydrofuran, preferably at an elevated temperature, to obtain formula V N-alkoxymethyl pyrroles. The reaction scheme is shown below in Flow Diagram II:

FLOW DIAGRAM II

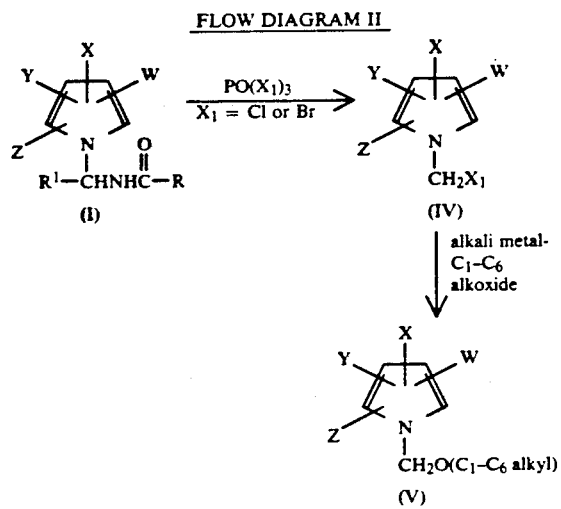

wherein W, X, Y, Z, $R_1$ and R are as described above for formula I.

In order to facilitate a further understanding of the invention, the following examples are presented primarily for the purpose of illustrating more specific details thereof. The invention is not to be deemed limited thereby except as defined in the claims.

EXAMPLE 1

Preparation of N-(hydroxymethyl)acetamide

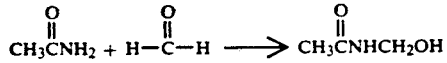

Acetamide (200 g, 3.4 mol) is added to a solution of potassium carbonate (20 g, 0.144 mol) in an aqueous formaldehyde solution (274 g, 37%, 3.4 mol). The reaction mixture is heated to 75° C., stirred for 3½ hours at room temperature, quenched with dry ice, diluted with acetone, dried with anhydrous sodium sulfate and filtered. The filtrate is dried with anhydrous sodium sulfate, filtered and concentrated in vacuo to give the title product as an oil (309 g) which is identified by ¹HNMR spectral analysis.

Following the above procedure, but substituting the appropriate amide for acetamide yields the following compounds: N-(hydroxymethyl)benzamide; N-(hydroxymethyl)-2-thiophenecarboxamide; N-(hydroxymethyl)-2,2-dimethylpropionamide; or 2,2,2-trifluoro-N-(hydroxymethyl)acetamide.

EXAMPLE 2

Preparation of N-(hydroxymethyl)acetamide acetate (ester)

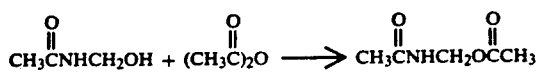

Acetic anhydride (25 g) and pyridine (10 drops) is added to N-(hydroxymethyl)acetamide (9 g, 0.1 mol). The reaction mixture is stirred overnight at room temperature, concentrated in vacuo and chased with xylene to give the title product as an oil (11.9 g, 0.9 mol) which is identified by ¹HNMR spectral analysis.

Following the above procedure, but substituting the appropriate N-(hydroxymethyl) compound for N-(hydroxymethyl)acetamide yields the following compounds: N-(hydroxymethyl)benzamide acetate (ester); N-(hydroxymethyl)-2-thiophenecarboxamide acetate (ester); N-(hydroxymethyl)-2,2-dimethylpropionamide acetate (ester); 2,2,2-trifluoro-N-(hydroxymethyl)-acetamide acetate (ester); N-(hydroxymethyl)-3-furamide acetate (ester); or N-(hydroxymethyl)-p-chlorobenzamide acetate (ester).

EXAMPLE 3

Preparation of N-{[2,3-dichloro-4-cyano-5-(3,4-dichlorophenyl)pyrrol-1-yl]methyl}acetamide

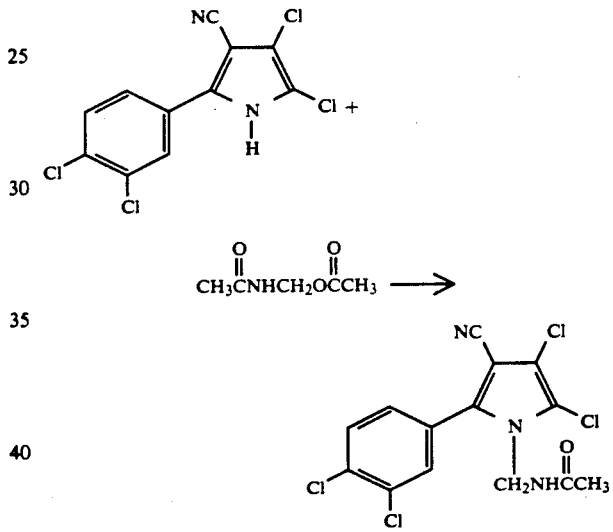

A slurry of 4,5-dichloro-2-(3,4-dichlorophenyl)pyrrole-3-carbonitrile (15.3 g, 0.05 mol) and tetrahydrofuran (80 mL) is cooled to 10° C. and treated portionwise over 20 minutes with sodium hydride (2.2 g, 60% in oil, 0.055 mol). After stirring for 15 minutes this solution is added dropwise to a 50° C. solution of N-(hydroxymethyl)acetamide acetate (ester) (9.18 g, 0.07 mol) and tetrahydrofuran (20 mL). The reaction mixture is refluxed for two hours, cooled to room temperature, diluted with water and extracted with ethyl acetate. The organic extract is washed with water, dried over anhydrous magnesium sulfate and concentrated in vacuo to give a solid. Flash chromatography of the solid on silica gel packed in methylene chloride using ethyl acetate/methylene chloride solutions as eluents gives a solid. Recrystallization of the solid from ethyl acetate gives the title product as off white crystals (5.35 g, mp 162°-162.5° C.) which is identified by IR and NMR spectral analyses.

Following the above procedure, but substituting the appropriate pyrrole for 4,5-dichloro-2-(3,4-dichlorophenyl)pyrrole-3-carbonitrile and N-(hydroxymethyl) acetate (ester) compound for N-(hydroxymethyl)acetamide acetate (ester) yields the following compounds.

N-{[3-bromo-5-(p-chlorophenyl)-4-cyano-2-(trifluoromethyl)pyrrol-1-yl]methyl}-2-thiophenecarboxamide, mp 180°-184° C.;

N-{[3-bromo-5-(p-chlorophenyl)-4-cyano-2-(trifluoromethyl)pyrrol-1-yl]methyl}pivalamide, mp 155°-157.5° C.;

N-{[3-bromo-5-(p-bromophenyl)-4-cyano-2-(trifluoromethyl)pyrrol-1-yl]methyl}benzamide, mp 159°-161° C.;

N-[(2,3,5-tribromo-4-cyanopyrrol-1-yl)methyl]pivalamide, mp 175°-180° C.;

N-[(2,3,5-tribromo-4-cyanopyrrol-1-yl)methyl]acetamide, mp 180°-185° C.;

N-{[3-bromo-5-chloro-4-cyano-2-(3,4-dichlorophenyl)-pyrrol-1-yl]methyl}benzamide, mp 175°-178.5° C.;

N-{[3-bromo-2-(3,4-dichlorophenyl)-4,5-bis(trifluoromethyl)pyrrol-1-yl]methyl}acetamide, mp 160.5°-163.5° C.;

N-{[3-bromo-5-(p-chlorophenyl)-4-cyano-2-(trifluoromethyl)pyrrol-1-yl]methyl)acetamide, mp 135°-136° C.;

N-{[2,4-dichloro-3-cyano-5-(3,4-dichlorophenyl)pyrroll-yl]methyl}acetamide, mp 146°-148° C.;

N-([2,4-bis(p-chlorophenyl)-3-nitro-5-(trifluoromethyl)-pyrrol-1-yl]methyl}acetamide, mp 187.0°-188° C.;

N-[(2,3,5-tribromo-4-cyanopyrrol-1-yl)methyl]benzamide, mp 168.5°-180.0° C.;

N-{[3-bromo-5-(p-chlorophenyl)-4-cyano-2-(trifluoromethyl)pyrrol-1-yl]methyl}benzamide, mp 153°-155° C.;

N-{[2,3-dichloro-4-cyano-5-(3,4-dichlorophenyl)pyrrol-1-yl]methyl}benzamide, mp 212°-215° C.;

N-{[3-bromo-5-(p-chlorophenyl)-4-cyano-2-(trifluoromethyl)pyrrol-1-yl]methyl}acetamide, mp 150.0°-150.5° C.; or N-{[3-bromo-5-(p-chlorophenyl)-4-cyano-2-(trifluoromethyl)pyrrol-1-yl]methyl}-2,2,2-trifluoroacetamide, mp 136.5°-138.0° C.

EXAMPLE 4

Preparation of
4,5-Dichloro-1-(chloromethyl)-2-(3,4-dichlorophenyl)-pyrrol-3-carbonitrile

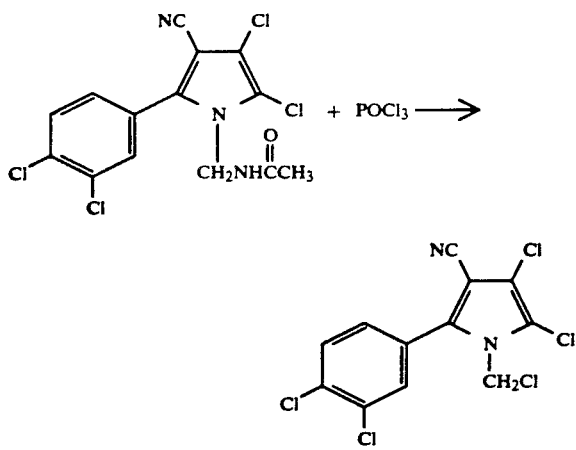

A mixture of N-{[2,3-dichloro-4-cyano-5-(3,4-dichlorophenyl)pyrrol-1-yl]methyl}acetamide (3.2 g, 0.0085 mol) and phosphorus oxychloride (6.51 g, 4 mL, 0.0424 mol) is heated at reflux temperature for 40 minutes, cooled, diluted with water and extracted with ethyl acetate. The combined organic extracts are washed sequentially with water and brine, dried over anhydrous magnesium sulfate and concentrated in vacuo to obtain a solid. Recrystallization of the solid from an ethyl acetate/heptane solution gives the title product as a pale brown solid (2.35 g, mp 153°-156.0° C.) which is identified by IR and NMR spectral analyses.

Following the procedure, but substituting the appropriate N-[(substituted pyrrol-1-yl)methyl]acetamide for N-{[2,3-dichloro-4-cyano-5-(3,4-dichlorophenyl)pyrrol-1-yl]methyl}acetamide and using either phosphorus oxychloride or phosphorus oxybromide yields the following compounds.

4-Bromo-1-(bromomethyl)-2-(p-chlorophenyl)-5-(trifluoromethyl)pyrrole-3-carbonitrile, mp 131.0°-135° C.;

4-bromo-1-(chloromethyl)-2-(p-chlorophenyl)-5-(trifluoromethyl)pyrrole-3-carbonitrile, mp 128.0-129.0; or 2,4,5-tribromo-1-(chloromethyl)pyrrole-3-carbonitrile, mp 117.0°-118.0° C.

EXAMPLE 5

Preparation of
4-Bromo-1-(ethoxymethyl)-2-(p-chlorophenyl)-5-(trifluoromethyl)pyrrole-3-carbonitrile

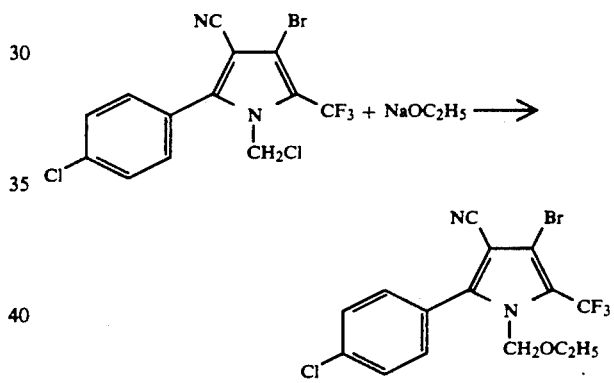

A solution of 4-bromo-1-(chloromethyl)-2-(p-chlorophenyl)-5-(trifluoromethyl)pyrrole-3-carbonitrile (2.0 g, 0.005 mol) in absolute ethanol is treated with a 21% wt/wt ethanolic solution of sodium ethoxide (0.36 g, 0.0053 mol), heated to 75°-80° C. for 20-30 minutes, cooled to room temperature and diluted with water and ether. The organic phase is dried over anhydrous magnesium sulfate and concentrated in vacuo to give a solid which is recrystallized form heptane to give the title product as a white solid (1.75 g, mp 97°-98° C.).

EXAMPLE 6

Insecticide and acaricide evaluations

The following tests show the efficacy of the compounds as insecticides and acarides. The evaluations are conducted with solutions of test compounds dissolved or dispersed in 50/50 acetone/water mixtures. The test compound is technical material dissolved or dispersed in said acetone/water mixtures in sufficient amount to provide the concentrations set forth in Table I below.

All concentrations reported herein are in terms of active ingredient. All tests are conducted in a laboratory maintained at about 27° C. The rating system employed is as follows:

| Rating System | |
|---|---|
| 0 = no effect | 5 = 56–65% kill |
| 1 = 10–25% kill | 6 = 66–75% kill |
| 2 = 26–35% kill | 7 = 76–85% kill |
| 3 = 36–45% kill | 8 = 86–99% kill |
| 4 = 46–55% kill | 9 = 100% kill |

The test species of insects used in the present evaluations along with specific test procedures are described below.

Spodoptera eridania 3rd instar larvae, southern armyworm

A sieva lima bean leaf expanded to 7 to 8 cm in length is dipped in the test suspension with agitation for 3 seconds and placed in a hood to dry. The leaf is then placed in a 100×10 mm petri dish containing a damp filter paper on the bottom and 10 3rd instar caterpillars. The dish is maintained for 5 days before observations are made of mortality, reduced feeding, or any interference with normal moulting.

Spodoptera eridania, 7-day residual

The plants treated in the above test are maintained under high intensity lamps in the greenhouse for 7 days. These lamps duplicate the effects of a bright sunny day and are kept on for 14 hour day length. After 7 days, the foliage is sampled and assayed as in the above-said test.

Tetranychus urticae (P-resistant strain), 2-spotted spider mite

Sieva lima bean plants with primary leaves expanded to 7 to 8 cm are selected and cut back to one plant per pot. A small piece is cut from a leaf taken from the main colony and placed on each leaf of the test plants. This is done about 2 hours before treatment to allow the mites to move over to the test plant and to lay eggs. The size of the cut piece is varried to obtain about 100 mites per leaf. At the time of the treatment, the piece of leaf used to transfer the mites is removed and discarded. The mite-infested plants are dipped in the test formulation for 3 seconds with agitation and set in the hood to dry. Plants are kept for 2 days before estimates of adult kill are made using the first leaf. The second leaf is kept on the plant for another 5 days before observations are made of the kill of eggs and/or newly emerged nymphs.

Empoasca abrupta, adults, western potato leafhopper

A Sieva lima bean leaf about 5 cm long is dipped in the test formulation for 3 seconds with agitation and placed in a hood to dry. The leaf is placed in a 100×10 mm petri dish containing a moist filter paper on the bottom. About 10 adult leafhoppers are added to each dish and the treatments are kept for 3 days before mortality counts are made.

Heliothis virescens, 3rd instart tobacco budworm

Cotton cotyledons are dipped in the test formulation and allowed to dry in a hood. When dry, each is cut into quarters and ten sections placed individually in 30 mL plastic medicine cups containing a 5 to 7 mm long piece of damp dental wick. One 3rd instar caterpillar is added to each cup and a cardboard lid placed on the cup. Treatments are maintained for 3 days before mortality counts and estimates of reduction in feeding damage are made.

Blattella germanica, residue test, adult male German cockroach

One mL of a 1000 ppm acetone solution of the test material is pipetted slowly over the bottom of a 150×15 mm petri dish so as to give as uniform coverage as possible. After the deposit has dried, 10 adult male cockroaches are placed in each dish and the lid is added. Mortality counts are made after 3 days.

The data obtained for the above described evaluations are reported in Table I.

TABLE I

| | Insecticide And Acaricide Evaluations | | | | | |
|---|---|---|---|---|---|---|
| | Southern Armyworm | | P. Res mite | Leaf-hopper | Tobacco Budworm | G. Cockroach (Residual) |
| Compound | (ppm) 1000 | 7 days | (ppm) 300 | (ppm) 100 | (ppm) 1000 | (ppm) 1000 |
| N-{[3-bromo-5-(p-chlorophenyl)-4-cyano-2-(trifluoromethyl)-pyrrol-1-yl]methyl}pivalamide | 9 | 9 | 7 | 9 | 9 | 5 |
| N-{[3-bromo-5-(p-bromophenyl)-4-cyano-2-(trifluoromethyl)-pyrrol-1-yl]methyl}benzamide | 9 | 9 | 9 | 9 | 9 | 9 |
| N-[(2,3,5-tribromo-4-cyano-pyrrol-1-yl)methyl]acetamide | 9 | 9 | 9 | 0 | 5 | 0 |
| N-[(2,3,5-tribromo-4-cyano-pyrrol-1-yl)methyl]pivalamide | 9 | 9 | 0 | 0 | 0 | 6 |
| N-{[3-bromo-5-chloro-4-cyano-2-(3,4-dichlorophenyl)pyrrol-1-yl]methyl}benzamide | 9 | 9 | 0 | 0 | 7 | — |
| N-{[3-bromo-2-(3,4-dichlorophenyl)-4,5-bis(trifluoromethyl)pyrrol-1-yl]methyl}-acetamide | 9 | — | 0 | 8 | 9 | — |
| N-{[2,4-dichloro-3-cyano-5-(3,4-dichlorophenyl)pyrrol-1-yl]methyl}acetamide | 9 | 9 | 5 | 0 | 9 | — |
| N-{[3-bromo-5-(p-chlorophenyl)-4-cyano-2-(trifluoromethyl)-pyrrol-1-yl]methyl}acetamide | 9 | 9 | 0 | 8 | 9 | — |
| N-{[2,4-bis(p-chlorophenyl)-3-nitro-5-(trifluoromethyl)-pyrrol-1-yl]methyl}acetamide | 9 | — | 0 | — | — | — |
| N-{[3-bromo-5-(p-chlorophenyl)- | 9 | 9 | 9 | 9 | — | 9 |

TABLE I-continued

| | Insecticide And Acaricide Evaluations | | | | | |
|---|---|---|---|---|---|---|
| | Southern Armyworm | | P. Res mite | Leaf- hopper | Tobacco Budworm | G. Cockroach (Residual) |
| Compound | (ppm) 1000 | 7 days | (ppm) 300 | (ppm) 100 | (ppm) 1000 | (ppm) 1000 |
| 4-cyano-2-(trifluoromethyl)-pyrrol-1-yl]methyl}acetamide | | | | | | |
| N-{[3-bromo-5-(p-chlorophenyl)-4-cyano-2-(trifluoromethyl)-pyrrol-1-yl]methyl}benzamide | 9 | 9 | 9 | 9 | 9 | 9 |
| N-{[2,3-dichloro-4-cyano-5-(3,4-dichlorophenyl)pyrrol-1-yl]methyl}benzamide | 9 | 9 | 0 | 0 | 9 | 0 |
| N-[(2,3,5-tribromo-4-cyano-pyrrol-1-yl)methyl]benzamide | 9 | 0 | 0 | 0 | 6 | 6 |
| N-{[2,3-dichloro-4-cyano-5-(3,4-dichlorophenyl)pyrrol-1-yl]methyl}acetamide | 9 | 9 | 0 | 4 | 9 | 2 |
| N-{[3-bromo-5-(p-chlorophenyl)-4-cyano-2-(trifluoromethyl)pyrrol-1-yl]methyl}-2-thiophenecarboxamide | 9 | 9 | 7 | 9 | 9 | 9 |

I claim:

1. A compound having the structural formula

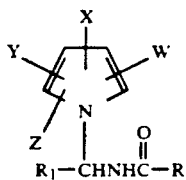

wherein
W is halogen, CN or $NO_2$;
X is halogen or phenyl optionally substituted with one or two halogen, CN, $NO_2$, $C_1$–$C_4$ alkyl, $C_1$–$C_4$ alkoxy or $CF_3$ groups;
Y is halogen, $CF_3$ or phenyl optionally substituted with one or two halogen, CN, $NO_2$, $C_1$–$C_4$ alkyl, $C_1$–$C_4$ alkoxy or $CF_3$ groups;
Z is halogen or $CF_3$;
$R_1$ is hydrogen or $C_1$–$C_4$ alkyl; and
R is $C_1$–$C_6$ alkyl optionally substituted with one to three halogen atoms,
phenyl optionally substituted with one or two halogen, CN, $NO_2$, $C_1$–$C_4$ alkyl, $C_1$–$C_4$ alkoxy or $CF_3$ groups,
2- or 3-thienyl or
2- or 3-furyl;
provided that when W is halogen, then X is phenyl optionally substituted with one or two halogen, CN, $NO_2$, $C_1$–$C_4$ alkyl, $C_1$–$C_4$ alkoxy or $CF_3$ groups and Y and Z are $CF_3$.

2. The compound according to claim 1 wherein
W is CN or $NO_2$;
X is phenyl optionally substituted with one or two halogen, CN, $NO_2$, $C_1$–$C_4$ alkyl, $C_1$–$C_4$ alkoxy or $CF_3$ groups;
Y is halogen or $CF_3$;
Z is halogen or $CF_3$;
$R_1$ is hydrogen; and
R is $C_1$–$C_6$ alkyl optionally substituted with one to three halogen atoms,
phenyl optionally substituted with one or two halogen, CN, $NO_2$, $C_1$–$C_4$ alkyl, $C_1$–$C_4$ alkoxy or $CF_3$ groups,
2- or 3-thienyl or
2- or 3-furyl.

3. The compound according to claim 2 wherein
X is phenyl optionally substituted with one or two halogen or $CF_3$ groups;
Y is Cl, Br or $CF_3$;
Z is Cl, Br or $CF_3$; and
R is $C_1$–$C_6$ alkyl optionally substituted with one to three halogen atoms,
phenyl optionally substituted with one or two halogen, $C_1$–$C_4$ alkyl, $C_1$–$C_4$ alkoxy or $CF_3$ groups,
or
2- or 3-thienyl.

4. The compound according to claim 3 N-{[3-bromo-5-(p-chlorophenyl)-4-cyano-2-(trifluoromethyl)pyrrol-1-yl]methyl}acetamide.

5. The compound according to claim 3 N-{[3-bromo-5-(p-chlorophenyl)-4-cyano-2-(trifluoromethyl)pyrrol-1-yl]methyl}benzamide.

6. The compound according to claim 3 N-{[3-bromo-5-(p-chlorophenyl)-4-cyano-2-(trifluoromethyl)pyrrol-1-yl]methyl}-2-thiophenecarboxamide.

7. The compound according to claim 3 N-{[2,3-dichloro-4-cyano-5-(3,4-dichlorophenyl)pyrrol-1-yl]methyl}acetamide.

8. A composition for controlling insects and acarina comprising an agronomically acceptable carrier and an insecticidally or acaricidally effective amount of a compound having the structural formula

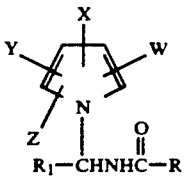

wherein
W is halogen, CN or $NO_2$;
X is halogen or phenyl optionally substituted with one or two halogen, CN, $NO_2$, $C_1$–$C_4$ alkyl, $C_1$–$C_4$ alkoxy or $CF_3$ groups;
Y is halogen, $CF_3$ or phenyl optionally substituted with one or two halogen, CN, $NO_2$, $C_1$–$C_4$ alkyl, $C_1$–$C_4$ alkoxy or $CF_3$ groups;
Z is halogen or $CF_3$;

$R_1$ is hydrogen or $C_1$-$C_4$ alkyl; and
$R$ is $C_1$-$C_6$ alkyl optionally substituted with one to three halogen atoms,
   phenyl optionally substituted with one or two halogen, CN, $NO_2$, $C_1$-$C_4$ alkyl, $C_1$-$C_4$ alkoxy or $CF_3$ groups,
2- or 3-thienyl or
2- or 3-furyl;
provided that when W is halogen, then X is phenyl optionally substituted with one or two halogen, CN, $NO_2$, $C_1$-$C_4$ alkoxy or $CF_3$ groups and Y and Z are $CF_3$.

* * * * *

UNITED STATES PATENT AND TRADEMARK OFFICE
CERTIFICATE OF CORRECTION

PATENT NO. : 5,130,328
DATED : July 14, 1992
INVENTOR(S) : Venkataraman Kameswaran It is certified that error appears in the above-indentified patent and that said Letters Patent is hereby corrected as shown below:

In Claim 8, column 14, line 5, after "$No_2$," the following should be inserted --$C_1 - C_4$ alkyl, --.

Signed and Sealed this

Sixth Day of August, 1996

Attest:

BRUCE LEHMAN

*Attesting Officer*  *Commissioner of Patents and Trademarks*